United States Patent [19]

Hayden

[11] Patent Number: 4,822,900

[45] Date of Patent: Apr. 18, 1989

[54] PRODUCTION OF ETHYLENE OXIDE

[75] Inventor: Percy Hayden, Guisborough, England

[73] Assignee: Imperial Chemical Industries PLC, London, England

[21] Appl. No.: 119,277

[22] Filed: Nov. 9, 1987

Related U.S. Application Data

[63] Continuation of Ser. No. 771,057, Aug. 30, 1985, abandoned.

[30] Foreign Application Priority Data

Sep. 12, 1984 [GB] United Kingdom ............... 8423044

[51] Int. Cl.$^4$ ............................................ C07D 301/10
[52] U.S. Cl. .................................... 549/534; 549/536; 549/537; 549/538
[58] Field of Search ................ 549/534, 536, 537, 583

[56] References Cited

U.S. PATENT DOCUMENTS

| | | |
|---|---|---|
| 2,279,470 | 4/1942 | Law et al. . |
| 4,130,570 | 12/1978 | Boreskov et al. ................. 549/535 |
| 4,356,311 | 10/1982 | Diamond et al. . |
| 4,419,276 | 12/1983 | Bhasin et al. ..................... 549/534 |

FOREIGN PATENT DOCUMENTS

| | | | |
|---|---|---|---|
| 486735 | 9/1952 | Canada ............................... 549/534 |
| 588750 | 12/1959 | Canada . |
| 3642 | 8/1979 | European Pat. Off. ........... 549/534 |
| 2936036 | 4/1981 | Fed. Rep. of Germany ...... 549/534 |
| 1600747 | 10/1981 | United Kingdom . |

OTHER PUBLICATIONS

H. K. Straschil et al, Engelhard Industries, Inc., Technical Bulletin, vol. 3(4), Mar. 1963, pp. 136–139.

Kirk-Othmer, Encyclopedia of Chemical Technology, 3rd ed., vol. 15, pp. 979–981, 983–984.

Nitroparaffins and Their Hazards, The National Board of Fire Underwriters (1959), pp. 7–59.

Primary Examiner—Richard I. Raymond
Attorney, Agent, or Firm—Cushman, Darby & Cushman

[57] ABSTRACT

Ethylene oxide is produced by contacting ethylene and oxygen in the presence of a chlorine containing reaction modifier with a silver containing catalyst, nitropropane being also present. The nitropropane raises the selectivity of the process.

10 Claims, No Drawings

PRODUCTION OF ETHYLENE OXIDE

This is a continuation of application Ser. No. 771,057, filed Aug. 30, 1985, which was abandoned upon the filling hereof.

This invention relates to the production of ethylene oxide.

In our European Pat. No. 3642 we disclosed a process of producing an olefin oxide which comprises contacting an olefine with oxygen in the presence of a silver-containing catalyst and a chlorine containing reaction modifier in which the performance of the catalyst was improved by contacting the catalyst also with a nitrate or nitrite forming substance which was in a gas phase. The use of numerous nitrate or nitrite forming substances was disclosed, but the use of NO and oxygen, $NO_2$ or $N_2O_4$ was preferred.

In most respects these materials, especially $NO_2$, are probably the best. However, because of the presence of water vapour in practical reaction conditions there is a tendency to produce corrosion in plants, especially if mists comprising nitric acid are produced.

We have also found that ethylene can react with oxides of nitrogen to form bi-isoxazoline which fouls feed lines under certain conditions. Also process control is complicated in that the analysis of streams containing oxides of nitrogen and water is difficult because, on cooling such streams, oxides of nitrogen are lost as condensate. It is thus difficult to obtain a representative analysis for the oxides of nitrogen under practical conditions at the inlet of a reactor if water-containing recycle streams are present (which is the normal industrial practise).

These problems may be reduced by feeding nitropropane to the process rather than oxides of nitrogen.

Our European Pat. No. 3642 discloses the use of lower nitro alkanes and mentions nitromethane in particular. However, nitromethane is subject to handling problemes, which are reviewed in the pamphlet "Nitroparaffins and their Hazards" by the Committee on Fire Prevention and Engineering Standards Research Division of the National Board of Fire Underwriters (1959) (USA). Nitromethane has been the subject of serious explosions and there are risks associated with lower nitro paraffins in general. We have preferred until recently to feed NO, $NO_2$ or $N_2O_4$ to the process directly despite the aforesaid disadvantages rather than to feed any of the substances referred to in out European Pat. No. 3642 which are capable of feeding nitrate and/or nitrite ions to the catalyst less directly by oxidation of such substances.

We have found that the nitropropanes are of remarkable effectiveness and give rise in general to less corrosion, do not form bi-oxazolines and are much more amenable to analysis in samples taken from the reactor inlet. We have also found that they can be handled with acceptable safety. The high efficiency of the nitropropanes in the process is surprising in view of the necessity of oxidising three carbon atoms per molecule before they are able to form nitrates or nitrites.

This invention comprises a process of producing ehtylene oxide by contacting ethylene and oxygen in the presence of a chlorine containing reaction modifier with a silver containing catalyst in which the performance of the catalyst is improved by contacting the catalyst also with a nitropropane. 1-nitropropane and/or preferably 2-nitropropane are used.

In general, the effect of the nitropropane is to increase the selectivity of the process.

By the selectivity of the catalyst is meant the proportion of the ethylene consumed which is converted to ethylene oxide in the process. The selectivity of silver-containing catalysts in the process may fall with prolonged use. Contacting used catalyst with a nitropropane tends to improve or at least partly to restore the selectivity of the catalyst, and continuously contacting the catalyst with a nitropropane in the process in general improves the selectivity of the catalyst or reduces the rate of loss of selectivity of the catalyst. Restoration of the selectivity of the catalyst may be carried out more than once if desired.

The following precautions should be taken in introducing a nitropropane to the process.

1. Pumping should be by a positive displacement pump which is provided with relief against pressures greater than 50 bars. The temperature of the nitropropane in the pump should not exceed 80° C. and is preferably below 50° C. and more preferably below 30° C..

2. the nitropropane should be introduced to a point in the process at which the temperature is at least 50° C. (to provide rapid evaporation) and at most 100° C., (as there is an increasing danger of detonation as the temperature is increased), and at which the pressure is at most 40 bars absolute.

3. The liquid nitropropane should not be contacted with an oxidising agent, which includes air, at a pressure greater than 40 bars. Suitably therefore unless the pump has relief at less than 40 bars no air should be allowed to enter the pump with the nitropropane.

The nitropropane should not be contaminated with alkalies, strongs acids or other materials likely to reduce its stability.

In order to provide rapid dispersion of nitropropane into the process gas without the back-up pressure and possibility of blockages attendant on spraying it as fine droplets from a nozzle it is preferred that it should be fed at as low a pressure as possible onto an inert porous material through which a substantial rate of process gas is maintained. The porous material should not itself present a major restriction to gas flow. A stainless steel mesh may be used.

If desired, a desensitising diluent for example toluene or a lower aliphatic alcohol may be added to the nitropropane. The nitropropane as introduced to the process should also be substantially free from water.

Provided that in all other respects the utmost care is taken in handling the nitropropane it is believed that the hazards may be reduced to acceptable levels by careful attention to the above matters, but users of the invention must be vigilant in all safety aspects and should make full use of any techniques which may now or in the future become available to improve safety.

The catalyst suitably comprises silver supported on a porous heat resisting support which has a specific surface area in the range 0.05 to $10 m^2/g$ and preferably 0.1 to 5 $m^2/g$ and more preferably 0.3 to 3 $m^2/g$ as measured by the Brunauer, Emmett and Teller method. The catalyst may be produced as disclosed in European Pat. No. 3642.

The catalyst support preferably has an apparent porosity as measured by the mercury absorption method of at least 20%, for example 25-70% preferably 30-65% and mean pore diameters of 0.1 to 20 microns preferably 0.3 to 4 microns as measured by the mercury porosimetry method. The pore size distribution of the support may be bi-or tri-modal, in which case the pores of diameters up to 2 microns preferably account for 30 to 70% of the total pore volume the pores of diameter 2 to 20 microns preferably 0 to 50% of the total pore volume.

Most of the silver content of the catalyst is preferably present in the form of discrete particles adhering to the support having equivalent diameters of less than 10,000A preferably in the range 20-10,000A and more preferably 40-8,000A for example 100-5,000A. By equivalent diameter is meant the diameter of a sphere of the same silver content as the particle.

Preferably at least 80% of the silver is present as particles having equivalent diameters in the aforesaid range, the quantity of silver being judged in terms of the number of particles falling in that range. The silver is believed to be present largely as metallic silver. The dimensions of the silver particles may be determined by scanning electron microscopy.

The support may be an alumina, silicon carbide, silica, zirconia, titania or silica/alumina support, but it is preferably composed of an aggregate of alpha-alumina particles which may be fused together or cemented together with, for example silica or baryta.

The catalyst preferably comprises 3 to 50% and more preferably 3 to 30% for example 6 to 28% by weight of silver.

It is preferred that the catalyst should contain cations, for example alkali and/or alkaline earth metal cations as the corresponding nitrate or nitrite or in a form capable of reacting to produce the corresponding nitrate or nitrite. This is especially preferred if the catalyst is treated with the nitrate or nitrite forming substance intermittently in order to restore its selectivity. It is believed that an effect of such cations is to hold more nitrate and/or nitrite ions on the catalyst or to hold them longer than is the case in their absence but we do not wish to be bound by any theory as to their action.

The cations may be introduced to the support before during or after the introduction of the silver compound. Preferably the cations are introduced to a support in which the silver is present in metallic form. The cations are suitably introduced as solutions in water and/or organic solvents. If it is desired to impregnate a catalyst which has already been used in the oxidation of an alkene to an alkylene oxide and has lost performance, this may be carried out also. Suitable concentrations of such cations in a form which is extractable by water may be for example 50 to 5000 parts per million of alkali metals by weight and/or 50 to 20,000 parts per million of alkaline earth metals by weight.

The cations may be provided for example as nitrates, hydroxides, carbonates, bicarbonates or carboxylates, for example lactates or more preferably oxalates.

The catalyst preferably contains rubidium, cesium, lithium, cadmium, calcium, magnesium, strontium, barium and/or sodium and/or more preferably potassium, these elements being present as compounds which are extractable from the catalyst by water.

Partial pressures of ethylene in processes according to the invention may be in the ranges 0.1-30 and preferably 1 to 30 bars. The total pressure may be in the range of from 1 to 100 and preferably 3-100 bars absolute. The molar ratio of oxygen to ethylene may be in the range 0.05 to 100. The partial pressure of oxygen may be in the range 0.01 and preferably 0.1 to 20 bars and preferably 1-10 bars. The oxygen may be supplied for example in the form of air or preferably as commercial oxygen. A diluent for example helium, nitrogen, argon, carbon dioxide and/or methane may be present in proportions of 10-80% and preferably 40-70% by volume in total. Suitably the diluent comprises methane as aforesaid together with, for example 100 to 20,000 parts per million by volume of ethane, preferably together with small amounts, for example 10 to 10,000 parts per million by volume of $C_3$ to $C_6$ alkanes, cycloalkanes or alkenes preferably propylene, cyclopropane, isobutene or isobutene. It is necessary to operate using gase compositions which are outside the explosive limits.

The temperature is suitably in the range 180° to 320° C., preferably 200° to 300° C. and more preferably in the range 220° to 290° C.. Contact times should be sufficient to convert 0.5-70%, for example 2 to 20 and preferably 5-20% of the ethylene and unconverted ethylene is, after separation of the product, suitably recycled, optionally in the presence of unconverted oxygen where appropriate and suitably after partial removal of $CO_2$. It is preferred that the average $CO_2$ content in the pores ie in contact with the catalyst should be in the range 1% to 7% andmore preferably 2% to 5% by volume.

The chlorine-containing reaction modifier may be of known type. It is preferred that it should be a $C_1$ to $C_{10}$ compound also containing hydrogen. It may be for example 1,1 or preferably 1,2-dichloroethane but it is preferred to use methyl chloride or more preferably vinyl chloride. Chlorinated aromatic compounds, for exaple chlorobenzene, dichlorobenzene and chlorinated toluenes are also suitable. It is preferred that the concentration of the chlorine containing reaction modifier should be in the range 0.1-500 and preferably 1 to 50 parts per million parts of the reaction medium by weight.

the nitropropane may be supplied continuously to the process at a low level for example 1 to 200 and preferably 5 to 100 parts per million of the process gas by volume. If it is desired to regenerate the catalyst intermittently the gas contacting the catalyst may contain much greater quantities of nitropropane together with sufficient oxygen to allow the production of the required nitrate or nitrite. Preferably the gas is flowed through the catalyst.

Improvement or restoration of the selectivity of a catalyst which has lost selectivity in the reaction may be carried out at a wide range of temperatures for example from 150° to 350° C. but temperatures of 200°-300° C. are preferred. The pressures may be in the range 0.1 to 100 bard but are preferably in the range 1-5 bars absolute.

Suitably in regeneration of the catalyst at least 20 and preferably at least 300 parts of nitrate and/or nitrite per million parts by weight of the catalyst are added.

Regeneration may be carried out in the presence of the reactants and under normal reaction conditions by introducing the nitrate or nitrite forming compound to the reaction and preferably maintaining in the catalyst a concentration of at least 20 and more preferably at least 300 parts of nitrate and/or nitrite per million parts by weight of catalyst.

EXAMPLE 1

A porous α-alumina carrier (supplied by Norton Company) and having a surface area of 0.5 $M^2g^{-1}$, a pore volume of 0.43 mls per gm, a $SiO_2$ content of 0.38%, and a sodium content of 121 ppm), in the form of rings of dimensions outer diameter 7.8 mm inner (hole) diameter 3.1 mm and thickness 7.8 diameter, was impregnated with a solution of silver nitrate dissolved in aqueous isopropylamine. The impregnated damp solid was pyrolysed by heating in a flow of nitrogen at up to 240° C.. the product was washed with hot water and dried. The dried catalyst was impregnated with an aqueous solution of potassium formate drained and dried. the final catalyst contained 16% w/w silver and 500 ppm of added potassium.

The catalyst was crushed and sieved to produce 112 g of particulate matter in the size range 1 to 3.35 mms. It was loaded into a stainless steel reactor of 10.8 mm internal diameter and 2,58 metres long. A gas mixture of ethylene (30%), oxygen (8%), carbon dioxide (2.5%) vinyl chloride (12 ppm), ethyl chloride (3 ppm) and 2 nitropropane (20 ppm) with nitrogen to balance was passed at a pressure of 15 bar gauge over the catalyst at a temperature of 252° C.. The gas was passed at a space velocity of 3070 $hr^{-1}$. The reaction produced ethylene oxide and carbon dioxide. Oxygen conversion was 20% and the selectivity of the snythesis of ethylene oxide was 87% (i.e. 87 moles of ethylene oxide were formed from 100 moles of ethylene converted).

EXAMPLE 2

Preparation of the Catalyst

Catalyst support pellets, comprising porous, high purity α-alumina containing 250±50 ppm of silica expressed as silicon and 40+10 ppm of sodium compounds expressed as sodium and 12+3 ppm of potassium compounds expressed as potassium in the form of cylinders 8 mm diameter and 8 mm pierced by seven longitudinal holes 1.22 mm in diameter one being central and the others being regularly spaced on a circle of 4.39 mm diameter centred on the axis of the pellet were uniformly coated with silver metal particles as described below. The mean pore diameter of porous alumina was 2-3 microns, its porosity as assessed by water absorption was 0.36±0.03 ml per g and its surface areas was about 0.5 $m^2$ per g.

Silver nitrate (4,418 g) was dissolved at 70° C. into distilled water (896 ml) and the resulting solution cooled to 50° C.. Monoisopropylamine (4,800 mls) was slowly added to this solution whilst stirring and cooling. The addition of the amine was sufficiently slow to avoid undue temperature rises. The temperature was maintained in the range 40° to 60° C.. The resulting clear solution was cooled to room temperature.

Support pellets (4,200 g) were evacuated and the solution of the silver nitrate-monoisopropylamine complex (5,000 mls) was added. After contacting the solution for 30 minutes, the impregnated pellets were separated from the residual solution and drained.

The support pellets, wet with the impregnated complex solution, were charged to a perforated basket which was then loaded into a reactor. The impregnated support was heated in a stream of hot nitrogen gas, the temperature was initially 100° C. and subsequently was gradually increased to 240° C. over a period of 18 hours. The impregnated complex decomposed to leave particulate silver evenly dispersed on the surface of the porous α-alumina pellets. The pellets also contained a residue of substances containing carbon and nitrogen.

The silver-coated pellet were subsequently contacted with hot air in a process which began by passing a stream of 5% air in nitrogen over the pellets heated at 150° C.. Subsequently the air content of the gas stream and the reactor temperature were gradually increased to 100% and 280° C., respectively. The rate of both changes were slow enough to avoid uncontrolled rises in temperature of the pellets due to the exothermicity of the process. On reaching 280° C., the pellets were contacted with the air stream for a further 2 hours and then allowed to cool.

The resulting silver-coated pellets, now substantially free of the residues of the silver nitrate - monoisopropylamine complex decomposition process were contacted with a flow of hot water in the temperature range 90° to 100° C. for 16 hours, then cooled, drained and dried by contacting with a stream of hot nitrogen at 150° C.. The product was a catalyst precursor and was characterised as a substantially clean, dry dispersion of silver particles evenly coated on the surfaces, both internal and external, of the porous 2-alumina pellets.

The catalyst precursor (4945 gm) was impregnated with potassium by being contacted at room temperature with 3323 mls of a solution of potassium formate in aqueous methanol.The aqueous methanol solvent contained 0.2% water by volume and 17.9 gms of potassium formate. The contacting was achieved by pumping the potassium formate solution through a bed of the catalyst precursor, collecting the liquor and recycling it through the bed for 16 hours. On completion of this impregnation stage, the catalyst pellets were drained and dried in a stream of warm nitrogen at 150° C.. The finished catalyst contained 500 to 600 ppm potassium.

This preparation was repeated to provide two additional batches of catalyst. The three batches were mixed and tested.

The catalyst was tested as follows. A reactor tube of 39 mm internal diameter was charged with the catalyst to give bed lengths of 10.7 m (bed volume 12.8 l.) and 3 m of tube length above the catalyst was packed with inert alumina pellets. The tube was surrounded by a liquid heat exchange fluid for temperature control. At start-up, a reactor feed gas composition of $O_2$ 6%, $C_2H_4$ 27%, vinyl chloride 6 ppm, ethane 0.1%, 2-nitropropane 20 ppm, the balance being substantially methane with a small proportion of inert gases, was fed. The feed to the reactor was at 75° C. and 18.5 bar pressure, with a gas hourly space velocity of 3600 $hr^{-1}$. Reactor temperatures were then raised to initiate reaction. Oxygen, ehtylene, ethane, methane, 2-nitropropane and vinyl chloride feeds were then mixed with recycle gas to give the desired feed composition. After twenty six days on line 1.03 $m^3$/hr oxygen, 1.4 $m^3$/hr ethylene, 6.8 l./hr ethane and 36 ml/hr vinyl chloride in methane all expressed as vapour at standard temperature and pressure plus an intermittent flow of methane sufficient to control the plant pressure plus 2-nitropropane were mixed with recycle gas. The 2-nitropropane was introduced by pumping liquid 2-nitropropane with a positive displacement micro pump having a relief valve set to operate at thirty bars. The temperature of 2-nitropropane in the pump was approximately 20° C. and it was substantially free from gaseous air, oxidising agents, alkalis, acids and water. It was introduced at a point in the process at which the temperature was 70° C., the pressure 18 bars absolute at 3.7 mls/hr of liquid onto a knitted stainless-steel mesh through which all the process gas was passed.

The reactor feed composition was analysed to be $O_2$ 7.5% $C_2H_4$ 27%, $CO_2$ 0.3%, vinyl chloride 7.2 ppm, ethyl chloride 0.9 ppm, ehtane 0.1%, 2-nitropropane 20 ppm, 0.12% water vapour and an estimated content of oxides of nitrogen of about 3 ppm the balance being substantially methane. Analysis was carried out from the reactor inlet and less inaccuracy of analysis was found due to condensation of water than that which had occurred when NO and $NO_2$ had been supplied instead of the 2-nitro propane. The reaction feed was at 75° C. and 18.5 bar with a gas hourly space velocity of 3600 $hr^{-1}$. the oxygen conversion across the reactor was 28%. The reaction give a selectivity of ethylene converted of 87%. The average catalyst temperature was 255° C.. The product gases were cooled to 75° C. before being contacted with 250.1/hr of water at 20° C., to absorb product ethylene oxide. The resulting gas stream was then split, part being contacted with 250.1/hr of 0.5% w/w caustic soda solution in a carbon dioxide scrubber. The scrubber gaseous product and the bypass stream were combined and then compressed to form the recycle gas stream. No solid deposits resulting from the reaction of nitropropane with ethylene occurred. (Deposits can occur under certain conditions between $NO/NO_2$ and ethylene even at embient tempertures.) NO corrosion was observed in the reactor feed section of the plant.

EXAMPLE 3

A catalyst similar to that of Example 2 but containing 300–330 ppm potassium was tested as follows. A reactor tube of 39 mm internal diameter was charged with the catalyst to give bed lengths of 10. m (bed volume 11.92 1.) and 3 m of tube length above the catalyst was packed with inert alumina pellets. The tube was surrounded by a liquid heat exchange fluid for temperature control. At start-up, a reactor feed gas composition of $O_2$ 6%, $C_2H_4$ 27%, vinyl chloride 6 ppm, ethane 0.1%, 2-nitropropane 41 ppm, the balance being substantially methane with a small proportion of inert gases, was fed. The feed to the reactor was at 75° C. and 18.5 bar pressure, with a gas hourly space velocity of 3600 hr-1. Reactor temperatures were then raised to initiate reaction. Oxygen, ethylene, ethane, methane, 2-nitropropane and vinyl chloride feeds were then mixed with recycle gas to give the desired feed composition. The 2-nitropropane was introduced by pumping liquid 2-nitropropane with a positive displacement micro pump having a relief valve set to operate at 30 bars. The temperature of 2-nitropropane in the pump was approximately 20° C. and it was substantially free from gaseous air, oxidising agents, alkalis, acids and water. It was introduced at a point in the process at which the temperature was 70° C., the pressure 18 bars absolute at 4.8 mls/hr of liquid onto a knitted stainless-steel mesh through which all the process gas was passed.

After fourteen days on line the reactor feed composition was analysed to be $O_2$ 8.2% $C_2H_4$ 27%, $CO_2$ 1%, vinyl chloride 5.9 ppm, ethyl chloride 0.8 ppm, ethane 0.1%, 2-nitropropane 32 ppm, $NO_2$ 8.3 ppm, NO 2.0 ppm, 0.12% water vapour, the balance being substantially methane. Analysis was carried out from the reactor inlet and less inaccuracy of analysis was found due to condensation of water than that which had occurred when NO and $NO_2$ had been supplied instead of the 2-nitro propane. The reaction feed was at 75° C. and 18.5 bar with a gas hourly space velocity of 3340 $hr^{-1}$. The oxygen conversion across the reactor was 28%. The reaction give a selectivity of ethylene converted of 84.2%. The average catalyst temperature was 250° C.. The product gases were cooled to 75° C. before being contacted with 250.1/hr of water at 20° C., to absorb product ethylene oxide. The resulting gas stream was then split, part being contacted with 250.1/hr of 0.5% w/w caustic soda solution in a carbon dioxide scrubber. The scrubber gaseous product and the bypass stream were combined and then compressed to form the recycle gas stream. No solid deposits resulting from the reaction of nitropropane with ethylene occurred. (Deposits can occur under certain conditions between $NO/NO_2$ and ethylene even at embient temperatures.) No corrosion was observed in the reactor feed section of the plant.

ppm means, in the case of liquids or solids, parts per million by weight and in the case of gases, parts per million by volume. Gas hourly space velocities are calculated as at 20° C. and atmospheric pressure.

Throughout this specification, pressures are absolute.

I claim:

1. A process of producing ethylene oxide comprising the steps of:
   contacting ethylene and oxygen in the presence of a chlorine containing reaction modifier with a silver containing catalyst; and
   improving the performance of the catalyst by contacting the catalyst also with nitropropane in which the nitropropane is pumped as a liquid at a temperature not exceeding 80° C. by a positive displacement pump in the substantial absence of oxidizing agents said pump being provided with relief against pressures greater than 50 bars and said nitropropane being introduced to the process at a point at which the temperature is in the range 50° to 100° C. and the pressure is at most 40 bars.

2. A process as claimed in claim 1 in which the catalyst comprises silver supported on a porous heat resisting support which has a specific surface area in the range 0.05 to 10 $m^2/g$, as measured by the Bruauer Emmett and Teller method and an apparent porosity as measured by the mercury absorption method of at least 20%.

3. A process as claimed in claim 1 in which the catalyst comprises silver deposited on an 2-alumina support and in which an alkaline earth and/or preferably an alkali metal is present in a form which is extractable from the catalyst by water.

4. A process as claimed in claim 1 in which liquid nitropropane is fed at as low a pressure as possible onto an inert porous material where said liquid nitropropane is vaporized, and through which a substantial rate of flow of process gas is maintained.

5. A process as claimed in claim 1 in which the partial pressure of ethylene is in the range 0.1 to 30 bars, the total pressure is in the range 1 to 100 bars, the partial pressure of oxygen in 0.01 to 20 bars, and the temperature is 180° to 320° C.

6. A process as claimed in claim 1 in which the chlorine containing reaction modifier is selected from the group consisting of dichloroethane, methyl chloride or vinyl chloride.

7. A process as claimed in claim 1 in which the average $CO_2$ content of gas in contact with the catalyst is in the range 1% to 7% by volume.

8. A process as claimed in claim 1 in which the nitropropane is 2-nitropropane.

9. A process of producing ethylene oxide comprising the steps of:
   contacting ethylene and oxygen in the presence of a chlorine containing reaction modifier with a silver containing catalyst; and improving the performance of the catalyst by contacting the catalyst also with nitropropane in which the nitropropane is pumped as a liquid at a temperature not exceeding 80° C. by a positive displacement pump in the substantial absence of oxidizing agents said pump being provided with relief against pressures greater than 50 bars, said nitropropane being introduced to the process at a point at which the temperature is in the range 50° to 100° C. and the pressure is at most 40 bars, and said nitropropane being fed at as low a pressure as possible onto an inert porous material through which a substantial rate of flow of process gas is maintained.

10. A process of producing ethylene oxide comprising the steps of:
   contacting ethylene and oxygen in the presence of a chlorine containing reaction modifier with a silver containing catalyst; and
   improving the performance of the catalyst by contacting the catalyst also with nitropropane at a concentration of 1-200 ppm by volume, in which the nitropropane is pumped as a liquid at a temperature not exceeding 80° C. by a positive displacement pump in the substantial absence of oxidizing agents said pump being provided with relief against pressures greater than 50 bars and said nitropropane being introduced to the process at a point at which the temperature is in the range 50° to 100° C. and the pressure is at most 40 bars.

* * * * *